(12) United States Patent
Lynn et al.

(10) Patent No.: US 9,265,936 B2
(45) Date of Patent: Feb. 23, 2016

(54) LEAD ASSEMBLY AND RELATED METHODS

(75) Inventors: Mark C Lynn, Circle Pines, MN (US);
Luis J. Morales Cardona, Isabela, PR (US); Peter Hall, Andover, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1532 days.

(21) Appl. No.: 12/437,470

(22) Filed: May 7, 2009

(65) Prior Publication Data

US 2009/0306753 A1 Dec. 10, 2009

Related U.S. Application Data

(60) Provisional application No. 61/051,275, filed on May 7, 2008.

(51) Int. Cl.
*A61N 1/05* (2006.01)

(52) U.S. Cl.
CPC ........ *A61N 1/0563* (2013.01); *A61N 2001/0578* (2013.01); *Y10T 29/49174* (2015.01); *Y10T 29/49224* (2015.01)

(58) Field of Classification Search
CPC ........... A61N 1/0563; Y10T 29/49224; Y10T 29/19174
USPC ......................................... 607/115, 122, 127
See application file for complete search history.

(56) References Cited

U.S. PATENT DOCUMENTS

| | | | |
|---|---|---|---|
| 5,433,742 A | 7/1995 | Willis | |
| 5,476,589 A | 12/1995 | Bacino | |
| 5,609,622 A | 3/1997 | Soukup et al. | |
| 5,689,598 A | 11/1997 | Dean, Jr. et al. | |
| 5,789,720 A * | 8/1998 | LaGally et al. | 219/121.64 |
| 5,802,042 A | 9/1998 | Natarajan et al. | |
| 5,803,928 A | 9/1998 | Tockman et al. | |
| 5,832,503 A | 11/1998 | Malik et al. | |
| 5,861,023 A | 1/1999 | Vachon | |
| 5,913,037 A | 6/1999 | Spofford et al. | |
| 5,964,793 A * | 10/1999 | Rutten et al. | 607/119 |
| 6,028,769 A | 2/2000 | Zurek | |
| 6,059,614 A | 5/2000 | Shelby et al. | |
| 6,148,237 A | 11/2000 | Das | |
| 6,222,852 B1 | 4/2001 | Gandy | |
| 6,393,472 B1 | 5/2002 | Anerousis et al. | |
| 6,430,621 B1 | 8/2002 | Srikanth et al. | |
| 6,493,591 B1 | 12/2002 | Stokes | |
| 6,505,081 B1 | 1/2003 | Das | |
| 6,533,779 B2 | 3/2003 | Kinsella et al. | |
| 6,560,236 B1 | 5/2003 | Varghese et al. | |
| 6,680,945 B1 | 1/2004 | Merchant et al. | |

(Continued)

OTHER PUBLICATIONS

Bodzinga, Anne, et al., "Interworking IPTV Services with IMS", Telecommunications Network Strategy and Planning Symposium 2006 pp. 1-5.

(Continued)

*Primary Examiner* — Niketa Patel
*Assistant Examiner* — William Levicky
(74) *Attorney, Agent, or Firm* — Faegre Baker Daniels LLP

(57) ABSTRACT

Defibrillator lead designs and methods for manufacturing a lead having a fibrosis-limiting material covering, a shocking coil electrode, and an implantable lead body are disclosed herein. The shocking coil electrode includes at least one laser welded portion.

20 Claims, 6 Drawing Sheets

(56) References Cited

U.S. PATENT DOCUMENTS

| | | | |
|---|---|---|---|
| 6,769,124 | B1 | 7/2004 | Schoening et al. |
| 6,876,667 | B1 | 4/2005 | Synnestvedt et al. |
| 6,885,657 | B1 | 4/2005 | Rabenko et al. |
| 6,968,237 | B2 | 11/2005 | Doan et al. |
| 6,978,185 | B2 | 12/2005 | Osypka |
| 7,013,182 | B1 | 3/2006 | Krishnan |
| 7,020,529 | B2 | 3/2006 | Krall et al. |
| 7,054,309 | B1 | 5/2006 | Hoot et al. |
| 7,079,902 | B2 | 7/2006 | Soukup et al. |
| 7,082,463 | B1 | 7/2006 | Bradley et al. |
| 7,099,158 | B1 | 8/2006 | Bjorklund |
| 7,139,818 | B1 | 11/2006 | Kinnear, Jr. et al. |
| 7,200,145 | B1 | 4/2007 | Edsall et al. |
| 7,212,868 | B2 | 5/2007 | McAuliffe et al. |
| 7,218,827 | B2 | 5/2007 | Vongseng et al. |
| 7,313,445 | B2 | 12/2007 | McVenes et al. |
| 7,366,573 | B2 | 4/2008 | Knapp et al. |
| 7,760,984 | B2 | 7/2010 | Solheid et al. |
| 7,801,133 | B2 | 9/2010 | Siegel |
| 7,826,463 | B2 | 11/2010 | Patel et al. |
| 7,945,164 | B2 | 5/2011 | Theodoras, II |
| 7,969,880 | B2 | 6/2011 | Yano et al. |
| 7,983,190 | B2 | 7/2011 | Hirota |
| 7,990,994 | B1 | 8/2011 | Yeh et al. |
| 8,059,558 | B2 | 11/2011 | Oman |
| 8,401,669 | B2 | 3/2013 | Lynn |
| 8,639,356 | B2 | 1/2014 | Arnholt |
| 2002/0147486 | A1 | 10/2002 | Soukup et al. |
| 2004/0167595 | A1 | 8/2004 | Tuominen |
| 2005/0228469 | A1* | 10/2005 | Zarembo et al. .............. 607/122 |
| 2006/0241734 | A1* | 10/2006 | Marshall et al. .............. 607/122 |
| 2006/0277603 | A1 | 12/2006 | Kelso et al. |
| 2006/0282144 | A1 | 12/2006 | Knapp et al. |
| 2007/0038278 | A1 | 2/2007 | Zarembo |
| 2008/0183261 | A1 | 7/2008 | Hammill et al. |
| 2008/0294158 | A1* | 11/2008 | Pappone et al. ................. 606/41 |
| 2009/0112300 | A1 | 4/2009 | Horn-Wyffels |
| 2009/0281607 | A1 | 11/2009 | Arnholt |
| 2009/0287285 | A1 | 11/2009 | Lynn |
| 2009/0287286 | A1 | 11/2009 | Lynn |
| 2009/0306753 | A1 | 12/2009 | Lynn et al. |
| 2009/0319014 | A1 | 12/2009 | Muecke et al. |
| 2011/0161360 | A1 | 6/2011 | Lundstrom |
| 2014/0109404 | A1 | 4/2014 | Arnholt |

OTHER PUBLICATIONS

Cohen, Reuven, et al., "Video-on-Demand Session Management", IEEE Journal on Selected Areas in Communications vol. 14, No. 6.
European Search Report issued in EP Application 06125497, Publication 1931085, mailed Jan. 9, 2009, 8 pages.
European Search Report issued in EP Application 07104707, Publication 1973269, dated Aug. 27, 2007, 7 pages.
International Search Report and Written Opinion for PCT/EP2007/063467, mailed Mar. 4, 2008, 7 pages.
International Search Report and Written Opinion for PCT/EP2008/053369, mailed Jul. 2, 2008, 10 pages.
International Search Report and Written Opinion for PCT/EP2008/056563, maded Aug. 21, 2008, 11 pages.
International Search Report and Written Opinion for PCT/EP2008/056565, mailed Jan. 19, 2009.
International Search Report and Written Opinion for PCT/EP2008/060384, maded Nov. 11, 2008, 10 pages.
International Search Report and Written Opinion for PCT/EP2008/061403, mailed Dec. 18, 2008, 12 pages.
International Search Report and Written Opinion for PCT/EP2008/063270, mailed Jan. 21, 2009, 8 pages.
International Search Report and Written Opinion for PCT/EP2008/063639, mailed Oct. 1, 2009, 7 pages.
International Search Report and Written Opinion for PCT/EP2008/063667, mailed Jul. 30, 2009, 9 pages.
International Search Report and Written Opinion Issued in PCT/US2009/002859, mailed Dec. 2, 2009, 17 pages.
International Search Report for PCT/EP2008/053374, mailed May 8, 2008, 8 pages.

* cited by examiner

LEAD ASSEMBLY AND RELATED METHODS

RELATED APPLICATIONS

This application claims the benefit under 35 U.S.C. 119(e) of U.S. Provisional Patent Application Ser. No. 61/051,275, filed on May 7, 2008, which is incorporated herein by reference in it entirety.

TECHNICAL FIELD

This document pertains generally to implantable defibrillator leads.

BACKGROUND

Cardiac and other defibrillation systems typically include an implantable medical device (IMD), such as a pulse generator, electrically connected to the heart by at least one implantable defibrillator lead. More specifically, an implantable defibrillator lead provides an electrical pathway between the EMD, connected to a proximal end of the lead, and cardiac tissue, in contact with a distal end of the lead. In such a manner, electrical stimulation (e.g., in the form of one or more shocks or countershocks) emitted by the IMD may travel through the implantable defibrillator lead and stimulate the heart via one or more exposed, helically wound shocking coil electrodes located at or near the lead distal end portion. Once implanted, the exposed shocking coil electrodes often become entangled with fibrosis (i.e., a capsule of inactive tissue which grows into the exposed coils) with the end result being that a chronically implanted lead can be extremely difficult to remove by the application of tensile force to the lead proximal end.

Over time, situations may arise which require the removal and replacement of an implanted defibrillator lead. As one example, an implanted defibrillator lead may need to be replaced when it has failed, or if a new type of cardiac device is being implanted which requires a different type of lead system. As another example, bodily infection or shocking coil electrode dislodgement may require the replacement of an implanted defibrillator lead. In such situations, the implanted defibrillator lead may be removed and replaced with one or more different implantable leads.

To allow for easier removal, some implantable defibrillator leads include a fibrosis-limiting material covering a portion of the one or more otherwise exposed shocking coil electrodes thereon. When subjected to shear loads, such as during lead implantation procedures, the fibrosis-limiting material may separate from the associated shocking coil electrode or the shocking coil electrodes themselves may separate from the lead body or deform, thereby leaving uncovered coils that are subject to future fibrotic entanglement.

SUMMARY

Certain examples include a lead comprising a lead body, at least one shocking coil electrode, and a fibrosis-limiting material. The lead body extends from a lead proximal end portion to a lead distal end portion and may optionally include an inner insulating layer and an outer insulating layer. At least one shocking coil electrode is disposed along the lead body, for example, but not limited to, at one or both of the lead intermediate portion or the lead distal end portion. The shocking coil electrode includes one or more welded portions, such as laser welded portions. The fibrosis-limiting material coaxially surrounds, at least in part, the at least one shocking coil electrode.

Another example includes a method of manufacturing the lead including forming a lead assembly including welding at least one electrode coil, and coating the at least one electrode coil and the welded portion with a coating of fibrosis limiting material. The method further includes coupling the at least one electrode coil with at least one conductor, and disposing insulative lead body over at least a portion of the at least one conductor and adjacent to the electrode coil and coating.

These and other examples, advantages, and features of the present leads and methods will be set forth in part in the detailed description, which follows, and in part will become apparent to those skilled in the art by reference to the following description of the present leads, methods, and drawings or by practice of the same.

BRIEF DESCRIPTION OF THE DRAWINGS

In the drawings, like numerals describe substantially similar components throughout the several views. Like numerals having different letter suffixes represent different instances of similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the present leads and methods may be practiced. These embodiments, which are also referred to herein as "examples," are described in enough detail to enable those skilled in the art to practice the present leads and methods. The embodiments may be combined, other embodiments may be utilized or structural or logical changes may be made without departing from the scope of the present leads and methods. The following detailed description is, therefore, not to be taken in a limiting sense, and the scope of the present leads and methods is defined by the appended claims and their legal equivalents.

In this document, the terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation.

Figure 1:
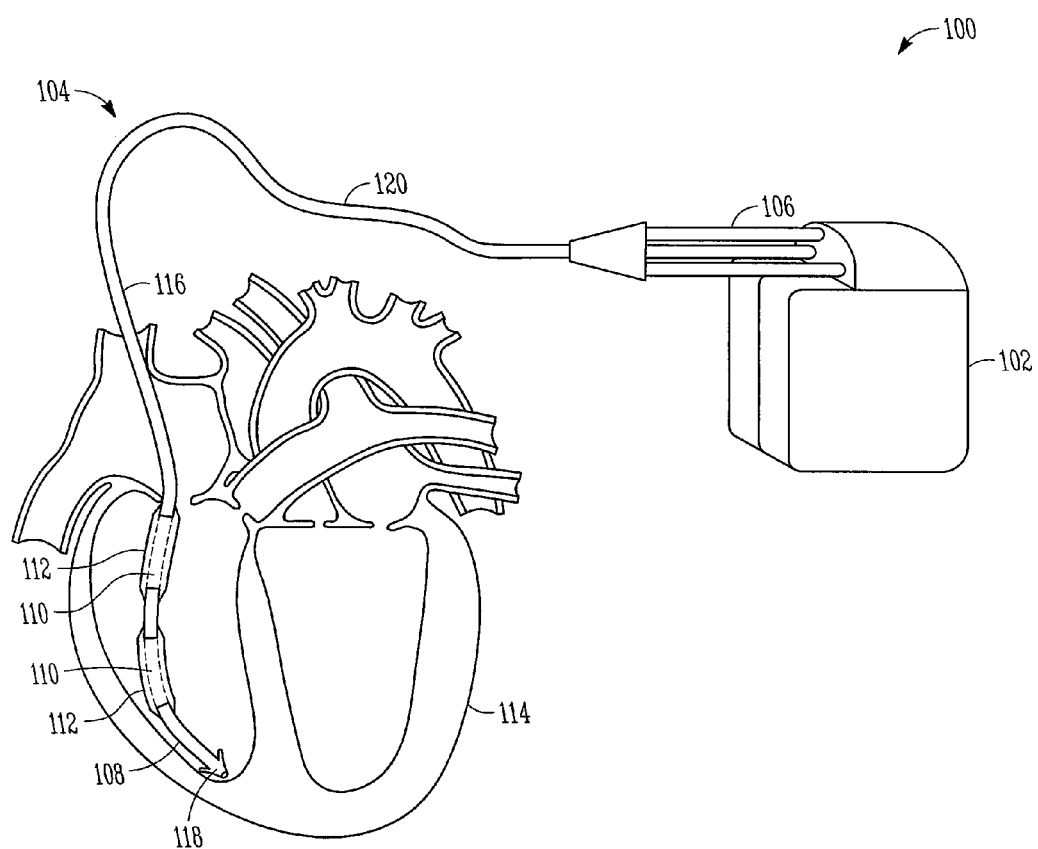
FIG. 1 illustrates a schematic view of a cardiac defibrillator system, including an implantable medical device and an implantable defibrillator lead, as constructed in accordance with at least one embodiment.

FIG. 1 illustrates a schematic view of a cardiac defibrillator system 100, which is useful for the correction of tachycardia or fibrillation, among other things. The system 100 includes an implantable medical device 102 and at least one implantable defibrillator lead 104. As shown, the implantable defibrillator lead 104 includes a lead body 120 extending from a lead proximal end portion 106, coupled with the implantable medical device 102, to a lead distal end portion 108 implanted within, on, or near a heart 114, with a lead intermediate portion 116 therebetween. The lead intermediate portion 116 or the lead distal end portion 108 includes at least one shocking coil electrode 110, wherein the at least one shocking coil electrode 110 is defined in part by a longitudinal axis. In this example, the at least one shocking coil electrode 110 is surrounded by a fibrosis-limiting material 112. In various examples, the fibrosis-limiting material 112 comprises a thin, polymeric layer coaxially surrounding and contacting an outer surface 370 (FIG. 3) of the helically wound shocking coil electrode 110.

The implantable defibrillator lead 104 transmits electrical signals between a selected location within, on, or about the heart 114 and the implantable medical device 102, such as to monitor the heart's 114 electrical activity at the selected location or to carry stimulation signals (e.g., one or more shocks or countershocks) to the selected location from the implantable medical device 102. The implantable defibrillator lead 104 may include a fixation assembly, such as one or more tines 118 or a helical coil, to anchor the lead distal end portion 118 at the selected location. The one or more tines 118 may be formed as part of the lead body 120, and thus may include a biocompatible lead body material, such as silicone rubber, polyurethane, polyimide, or a non-porous fluoropolymer. The fixation can be an active fixation assembly and/or a passive fixation assembly.

Figure 2:
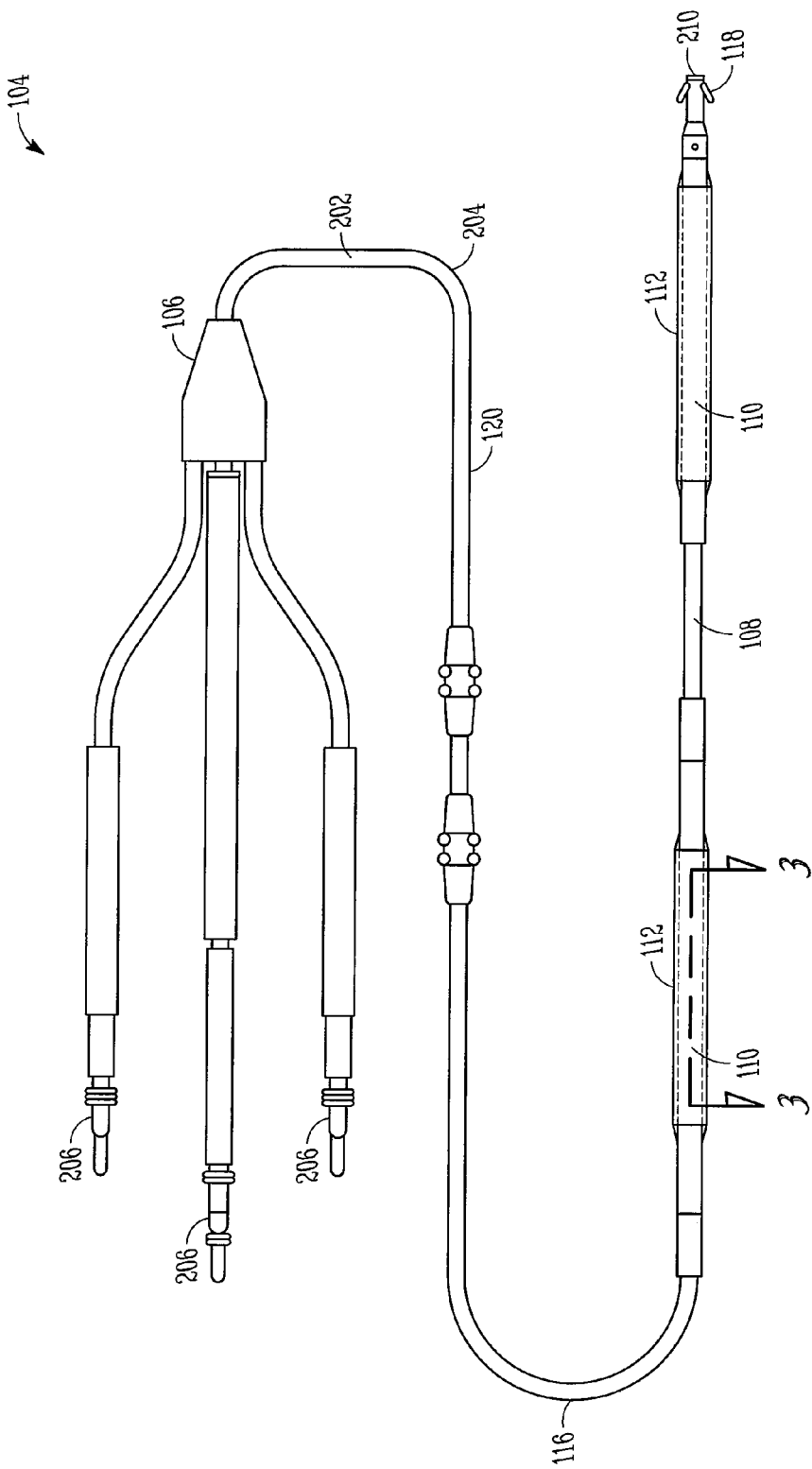
FIG. 2 illustrates a plan view of an implantable defibrillator lead, as constructed in accordance with at least one embodiment.

FIG. 2 illustrates a plan view of an implantable defibrillator lead 104, in one option. As shown, the implantable defibrillator lead 104 includes a lead body 120 extending from a lead proximal end portion 106 to a lead distal end portion 108 and having a lead intermediate portion 116 therebetween. In various examples, the lead body 120 includes an inner insulator layer 202, such as silicone rubber or other layer of impermeable polymeric electrically insulating material, and/or an outer insulator layer 204, such as polyurethane which provides high abrasion resistance.

In this example, the lead intermediate portion 116 and the lead distal end portion 108 include one or more shocking coil electrodes, such as a first and a second shocking coil electrode 110. The first and second shocking coil electrodes 110 include an uninsulated, helically wound shocking coil formed of a non-corrosive, bio-compatible metal, such as platinum, titanium, or alloys (e.g., platinum/iridium). The shocking coil electrodes 110 are covered by a pliable fibrosis-limiting material 112 (e.g., polytetrafluoroethylene (PTFE) or expanded PTFE (ePTFE)) in direct contact with an outer surface 370 (FIG. 3) of the shocking coil electrode 110. The implantable defibrillator lead 104 of this example further comprises an optional distal tip electrode 210. The distal tip electrode 210 may be porous and include a metallic mesh. One or more conductors in the lead body 120 electrically and mechanically couple the electrodes 110, 210 to the lead proximal end portion 106. The conductors may be of any structure or combination of structures, such as coaxial or coradial coils separated by an insulating tube, or side-by-side cables or coils separated by a polymer, such as fluoropolymer, silicone, polyimide, or polyurethane.

As shown in one option, the lead proximal end portion 106 includes one or more terminal leg connections 206 each of which is sized and shaped to couple to respective connector cavities incorporated into a header of the implantable medical device 102 (FIG. 1). It is through the coupling between the lead proximal end portion 206 and the connector cavities that the electrodes 110, 210 are electrically coupled to electronic circuitry within the implantable medical device 102. While FIG. 2 illustrates an implantable defibrillator lead 104 having three terminal connections 206 and three electrodes 110, 210, the present leads may vary, such as by including more or less than three terminal connections 206 and electrodes 110, 210.

Figure 3:
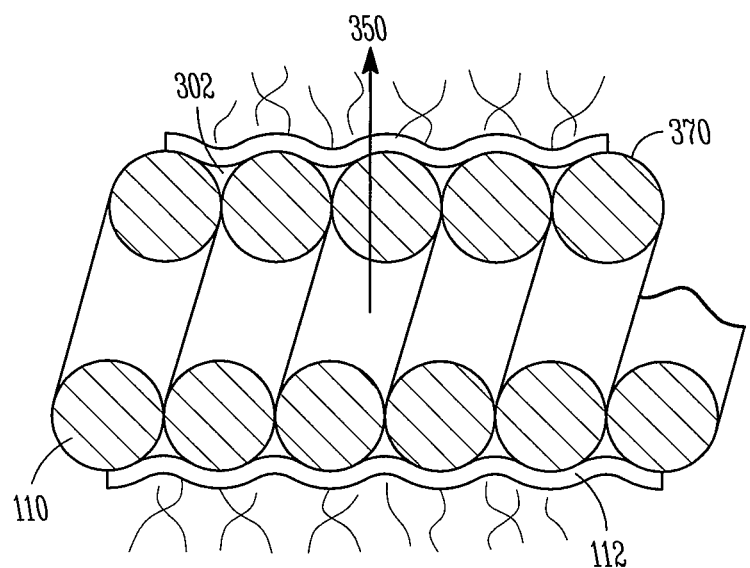
FIG. 3 illustrates an enlarged cross-sectional view of a portion of an implantable defibrillator lead, such as along line 3-3 of FIG. 2, and an implanted environment, as constructed in accordance with at least one embodiment.

FIG. 3 illustrates an enlarged cross-sectional view, such as along line 3-3 of FIG. 2, of a shocking coil electrode 110 surrounded by a thin, fibrosis-limiting material 112. As shown in this example, the fibrosis-limiting material 112 may be drawn into the coil gaps 302, such as via a heat sintering process, thereby eliminating or reducing the air volume present in the gaps. This tight conformation between the fibrosis-limiting material 112 and the shocking coil electrode 110 results in good electrical energy transmission 350 from the coil 110 to surrounding cardiac tissue. The use of the fibrosis-limiting material 112 as the tissue contacting portion of the shocking coil electrode 110 assists in preventing fibrotic tissue ingrowth.

Options for the fibrosis-limiting material 112 are as follows. For instance, the fibrosis-limiting material 112 may include PTFE, ePTFE, or other non-biodegradable and biocompatible materials, such as expanded ultra-high molecular weight polyethylene (eUHMWPE); may either be porous or non-porous; or may be inherently conductive or rely on porosity in conjunction with bodily fluids to be conductive. In various porous examples, the pore size is adequately small to allow penetration of conductive bodily fluids while substantially precluding tissue ingrowth, thus allowing a less traumatic removal of the defibrillator lead 104 after implantation should extraction become necessary. In various other examples, electrical conductivity through the fibrosis-limiting material 112 is not based on porosity, but rather is inherent in the material 112 as described in commonly-assigned Krishnan, U.S. Pat. No. 7,013,182 titled "CONDUCTIVE POLYMER SHEATH ON DEFIBRILLATOR SHOCKING COIL," which is hereby incorporated by reference in its entirety. In a further example, the fibrosis-limiting material 112 is wrapped around the coil electrode, for example, out of one or more strands of material.

Turning now to FIGS. 4A-4D, various techniques for manufacturing a lead having fibrosis-limiting material 112 are disclosed. These figures illustrate an side view of a portion of an implantable defibrillator lead 104, such as a shocking coil electrode 110, and a fibrosis-limiting material 112.

Figure 4A:
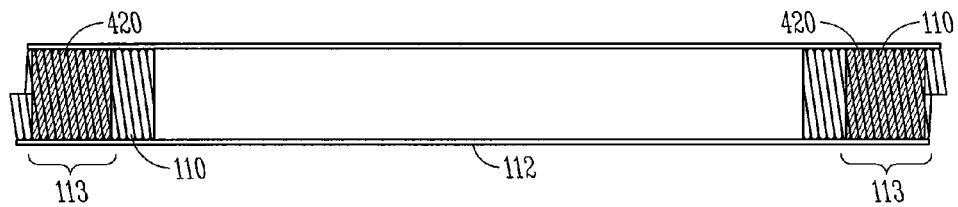
FIGS. 4A-4D illustrate a side view of a portion of an implantable defibrillator lead, as constructed in accordance with various embodiments.
Figure 4B:
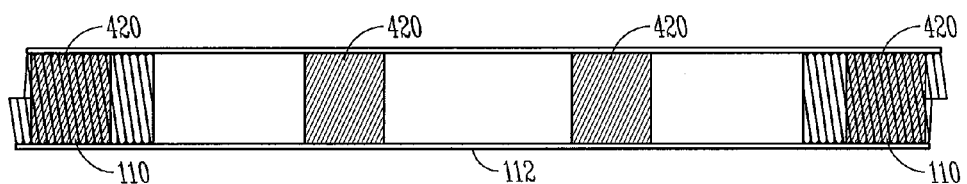
Figure 4C:
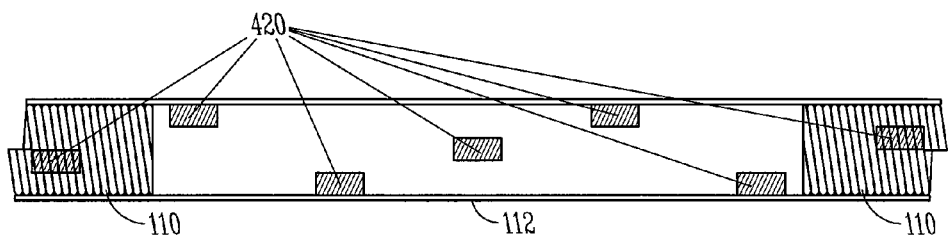

In an option, the shocking coil electrode 110 includes at least one laser weld portion 420. The at least one laser weld portion 420 is formed, for example, by laser welding the shocking coil electrode 110, for example, with a laser band that extends 360 degrees around the shocking coil electrode 110. In an option, the at least one laser weld portion 420 is included at one or more end portions 113 of the shocking coil electrode 110. In a further option, the laser weld portion is formed on one or more filars of the shocking coil electrode 110. For example, the laser weld portion is formed, in an option, two or more filars of the shocking coil electrode 110, and in another option on 8-12 filars of the shocking coil electrode 110. In another option, about 5 mm of the shocking coil electrode 110 is formed inflexible, for example with the laser weld. In a further option, the filars are close wound coils. In a further option, multiple portions of the shocking coil electrode 110 can include laser weld portions 420, such as shown in FIGS. 4A, 4B, and 4C. For instance, the laser weld portions 420 can be helically disposed about the coil 110, and/or multiple discrete portions can be disposed about the coil 110.

In an option, end portions of the shocking coil electrode 110 include the laser weld, and additional discrete portions include the laser weld portion 420. The laser weld portions 420 can extend partially around the shocking coil electrode 110, or can extend 360 degrees around the shocking coil electrode 110. In a further option, for instance as shown in FIG. 4C, multiple discrete laser weld portions 420 can be included in a pattern along the shocking coil electrode 110, or can be randomly disposed along the shocking coil electrode 110.

The fibrosis-limiting material 112 coaxially covers the shocking coil electrode 110 and the laser weld portions 420 in a tightly conforming manner, in an option, and the laser weld portion 420 improves adhesive of the fibrosis limiting material 112 to the shocking coil electrode 110. For instance, the laser weld creates a relatively smooth surface for the fibrosis limiting material to attach to. In an option, the fibrosis-limiting material 112 extends to the ends of the shocking coil electrode 110. In a further option, the fibrosis limiting material 112 extends to less than a length of the shocking coil electrode 110. In yet another option, the fibrosis limiting material 112 extends to greater than a length of the shocking coil electrode 110.

Figure 4D:
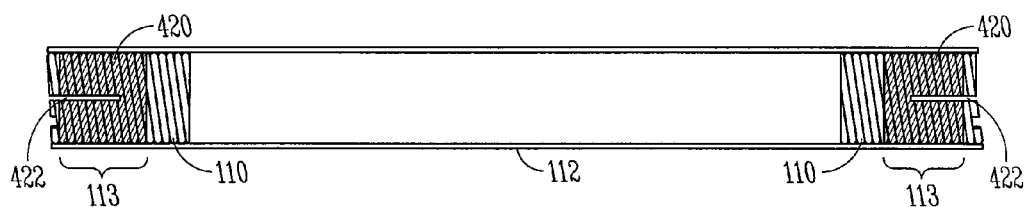

In a further option as shown in FIG. 4D, the laser weld portion 420 is at one more end portions 113 of the shocking coil electrode 110, and in an option is at each of the end portions 113 of the shocking coil electrode 110. The laser weld portion 420 includes at least one slit 422 therein, and in an option the at least one slit 422 is provided at each of the end portions 113. In an option, the at least one slit 422 includes two slits formed, for example, on opposite sides of the shocking coil electrode 110. The slit 422 allows for the shocking coil electrode 110 and/or the laser weld portion 420 to radially expand, for example, by 0.005-0.010 inches.

Figure 5:
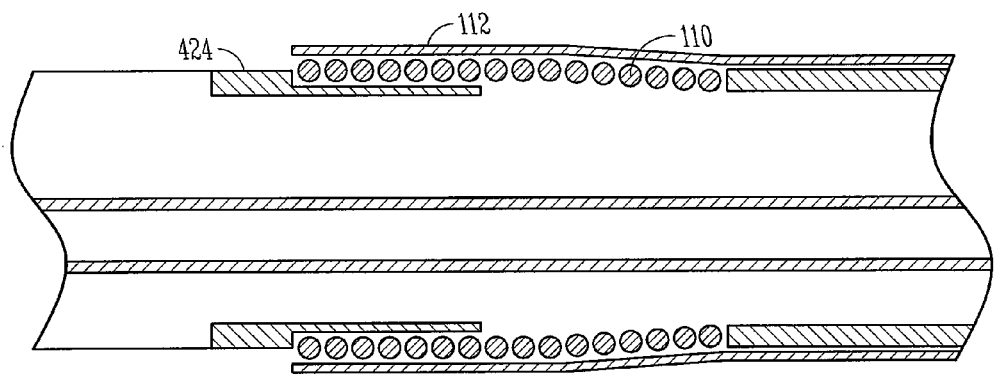
FIG. 5 illustrates a cross-sectional view of a portion of a lead, as constructed in accordance with at least one embodiment.

Referring to FIGS. 4D and 5, the fibrosis-limiting material 112 is disposed over the laser band portion 420 and the shocking coil electrode 110 after the at least one slit 422 is formed in the laser band portion 420. The shocking coil electrode 110 can be expanded to fit over a fitting 424 via the at least one slit 422, and he expanded shocking coil electrode 110 puts radial tension in the fibrosis-limiting material 112, such as ePTFE, and increases resistance of movement of the fibrosis-limiting material 112 relative to the shocking coil electrode 110, and/or increases the adhesion between the fibrosis limiting material and the shocking coil electrode 110.

Figure 6:
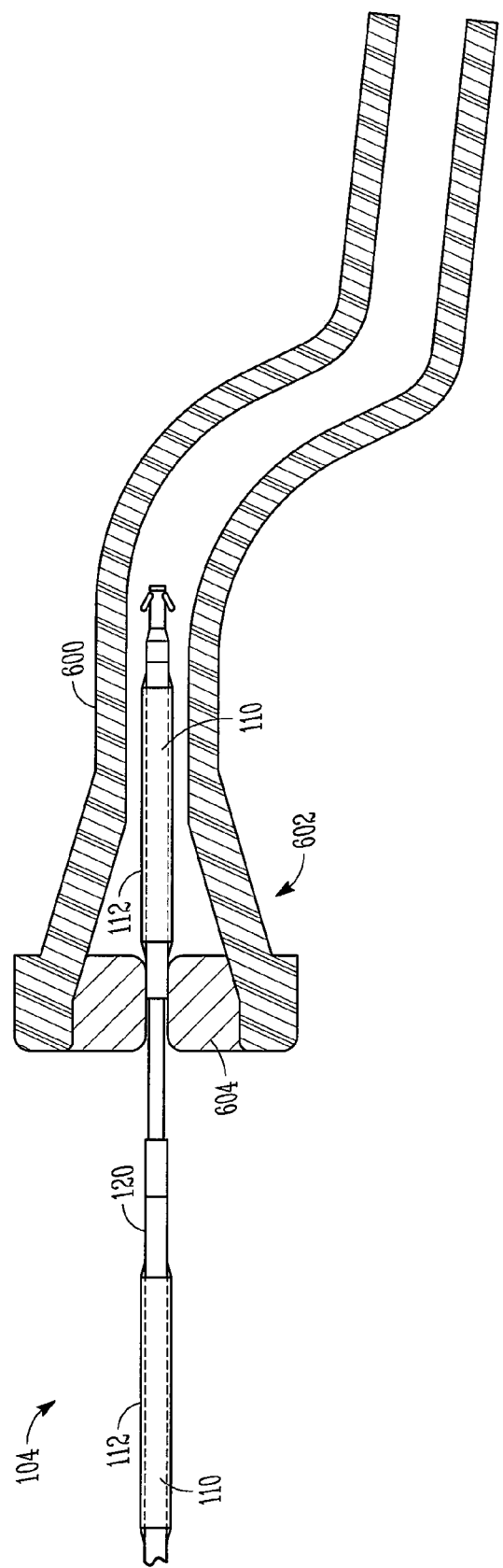
FIG. 6 illustrates a schematic view of an implantable defibrillator lead being advanced through an introducer sheath (shown in cross-section), as constructed in accordance with at least one embodiment.

Implantable defibrillator leads 104 are placed in contact with cardiac tissue by passage through a venous access, such as the subclavian vein, the cephalic vein, or one of its tributaries. In such a manner, an implantable defibrillator lead 104 may advantageously be placed in contact with the heart 114 (FIG. 1) without requiring major thoracic surgery. Instead, an implantable defibrillator lead 104 may be introduced into a vein and maneuvered therefrom into contact with the heart 114 or tissue thereof. A multi-step procedure is often required to introduce implantable defibrillator leads 104 within the venous system. Generally, this procedure consists of inserting a hollow needle into a blood vessel, such as the subclavian vein. A guide wire is then passed through the needle into the interior portion of the vessel and the needle is withdrawn. As illustrated in FIG. 6, an introducer sheath 600 with a dilator assembly 602 may be inserted over the guide wire into the vessel for lead 104 introduction. The sheath 600 is advanced to a suitable position within the vessel, such that a distal end thereof is well within the vessel, while a proximal end thereof is outside the patient.

When a physician implants a defibrillator lead 104, such as through the introducer sheath 600 and specifically an introducer seal 604, high drag forces may be created along the lead body 120. As a result of these high drag forces, previous lead component interfaces including the fibrosis-limiting material 112 to shocking coil electrode 110 and the shocking coil electrode 110 to the lead body 120 could separate or shift relative to one another leaving uncovered coil portions subjected to future fibrotic entanglement (e.g., the shocking coil electrode 110 became stretched, which in turn pulled the fibrosis-limiting material 112 away from the coil 110 and exposed a portion of the coil to fibrotic growth). Using the present lead manufacturing techniques, it has been found that such separating or shifting between the fibrosis-limiting material 112, the shocking coil electrode 110, and the lead body 120 is reduced or eliminated, thereby preventing fibrotic entanglement and facilitating lead extraction should it become necessary. The electrode coil 110 and the fibrosis-limiting material 112 of the lead 104 can withstand a drag force of about 0.5 to 1.0 pounds.

A method of manufacturing an implantable defibrillator lead including robust attachment between a fibrosis-limiting material, a shocking coil electrode, and a lead body is described herein. The lead assembly is formed including laser welding at least a portion of at least one electrode coil, for example, but not limited to at one or more ends of the coil, and/or at one or more discrete locations of the coil, and/or helically along the coil, and/or around 360 degrees around the coil. The laser welding can be done in the various embodiments discussed above, and/or illustrated in the drawings. In a further option, one or more slits are formed in the laser welded portions, for example with two slits.

A fibrosis-limiting material is coated, for example coaxially fitting the material over at least one shocking coil electrode. In various examples, this coaxially fitting includes positioning a portion of the fibrosis-limiting material proximal or distal to a shocking coil electrode end. The fibrosis-limiting material is formed onto an outer surface of the at least one shocking coil electrode, such as through the use of heat. One or more portions, such as end portions, of the at least one shocking coil electrode are coupled to a lead body or component. Optionally, the coupling between the shocking coil electrode and the lead body includes the use of an adhesive.

It is to be understood that the above description is intended to be illustrative, and not restrictive. For instance, any of the aforementioned examples may be used individually or with any of the other examples. In addition, the aforementioned examples may or may not include the use of adhesives (e.g., medical adhesives) for selected component attachment. Many other embodiments may be apparent to those of skill in the art upon reviewing the above description. The scope of the present leads and methods should, therefore, be determined with reference to the appended claims, along with the full scope of legal equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, assembly, article, or process that includes elements in addition to those listed after such a term in a claim are still deemed to fall within the scope of such claim.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A lead assembly comprising:
    a lead body including elongate tubing extending from a first end portion to a second end portion and having an intermediate portion therebetween;
    at least one electrode coil disposed along the lead body;
    the at least one electrode coil comprising a plurality of filars and having at least one laser weld portion formed of two or more of the filars; and
    at least one coating disposed along the at least one electrode coil including the at least one laser weld portion, the at least one electrode coil is defined in part by a longitudinal axis;
    wherein the at least one laser weld portion forms a surface for promoting adhesion of the at least one coating to the at least one electrode coil.

2. The lead assembly as recited in claim 1, wherein the at least one laser weld portion is in a helical pattern around the at least one electrode coil.

3. The lead assembly as recited in claim 2, wherein multiple discrete weld portions are disposed in a helical pattern around the at least one electrode coil.

4. The lead assembly as recited in claim 2, wherein the helical pattern is a continuous helical weld around the longitudinal axis of the at least one electrode coil.

5. The lead assembly as recited in claim 1, wherein the weld portion encircles at least a portion of the at least one electrode coil.

6. The lead assembly as recited in claim 5, wherein the weld portion encircles around 360 degrees around a perimeter of the at least one electrode coil.

7. The lead assembly as recited in claim 1, further comprising at least one slit in the laser weld portion.

8. The lead assembly as recited in claim 1, wherein multiple weld portions are disposed along the at least one electrode coil.

9. A lead assembly comprising:
    a lead body including elongate tubing extending from a first end portion to a second end portion and having an intermediate portion therebetween;
    at least one electrode coil disposed along the lead body, the electrode coil comprising a plurality of filars and including end portions;
    the at least one electrode coil having at least one laser weld portion formed of two or more of the filars in at least one end portion; and
    at least one coating disposed along the at least one electrode coil including the at least one laser weld portion, the at least one electrode coil is defined in part by a longitudinal axis;
    wherein the at least one laser weld portion forms a surface for promoting adhesion of the at least one costing to the at least one electrode coil.

10. The lead assembly as recited in claim 9, wherein the least one laser weld portion is a laser band.

11. The lead assembly as recited in claim 10, wherein the laser band is at each end portion of the at least one electrode coil.

12. The lead assembly as recited in claim 9, further comprising at least one slit in the laser weld portion.

13. The lead assembly as recited in claim 12, wherein the at least one slit is disposed at an end portion of the at least one electrode coil.

14. A method comprising:
    forming a lead assembly including at least one electrode coil comprising a plurality of filars by welding two or more of the filars of the at least one electrode coil to form at least one welded portion, coating the at least one electrode coil and the at least one welded portion with a coating of fibrosis limiting material;
    coupling the at least one electrode coil with at least one conductor; and
    disposing an insulative lead body over at least a portion of the at least one conductor and adjacent to the at least one electrode coil and coating;
    wherein the at least one welded portion forms a surface for promoting adhesion of the coating to the at least one electrode coil.

15. The method as recited in claim 14, wherein welding the at least one electrode coil includes welding one or more end portions of the at least one electrode coil.

16. The method as recited in claim 15, further comprising forming at least one slit in the welded portions.

17. The method as recited in claim 15, wherein welding the at least one electrode coil further comprises laser banding two or more filars together.

18. The method as recited in claim 15, wherein welding the at least one electrode coil includes welding the electrode coil in a helical pattern around the at least one electrode coil.

19. The method as recited in claim 15, wherein welding the at least one electrode coil includes welding the electrode coil in multiple discrete weld portions in a discrete helical pattern around the at least one electrode coil.

20. The method as recited in claim 15, wherein welding the at least one electrode coil includes laser welding the electrode coil.

* * * * *